United States Patent [19]

Roy et al.

[11] 4,223,016
[45] Sep. 16, 1980

[54] PEPTIDES

[75] Inventors: Peter Roy, Cowfield; Brian G. Overell, Dorking; Denis R. Stanworth, Malvern, all of England

[73] Assignee: Beecham Group Limited, United Kingdom

[21] Appl. No.: 920,151

[22] Filed: Jun. 29, 1978

[30] Foreign Application Priority Data

Jun. 29, 1977 [GB] United Kingdom ............... 27140/77

[51] Int. Cl.$^2$ ..................... A61K 37/00; C07C 103/52
[52] U.S. Cl. ............................... 424/177; 260/112.5 R
[58] Field of Search .................. 260/112.5 R; 424/177

[56] References Cited

U.S. PATENT DOCUMENTS

| | | | |
|---|---|---|---|
| 3,374,218 | 3/1968 | Bernardi et al. | 260/112.5 R |
| 3,479,333 | 11/1969 | Greven | 260/112.5 R |
| 3,832,337 | 8/1974 | Ondetti et al. | 260/112.5 R |
| 3,864,481 | 2/1975 | Hashim | 260/112.5 R |
| 4,059,693 | 11/1977 | Stewart | 260/112.5 R |
| 4,086,219 | 4/1978 | Wittle et al. | 260/112.5 R |
| 4,087,419 | 5/1978 | Tinney | 260/112.5 R |
| 4,107,298 | 8/1978 | Luning | 260/112.5 R |
| 4,113,858 | 9/1978 | Hashim | 260/112.5 R |

OTHER PUBLICATIONS

Bach, Academie des Sciences (1976), 1605–1609, vol. 283.
J. Med. Chem. (1970) 13, 4 pp. 744 & 745.
Liebigs Ann. Chem. Bd. 681, 1964, pp. 241–249.
C & E News (1963), pp. 44–45.

Primary Examiner—Delbert R. Phillips
Attorney, Agent, or Firm—Jacobs & Jacobs

[57] ABSTRACT

Peptides (6–12 amino acids) and their salts, useful in allergy desensitization compositions, particularly vaccines, have the formula $$X-R-R_1-R_2-R_3-Y$$

where R is optional and, if present, is a group resistant to enzyme hydrolysis; $R_1$ is a basic amino acid residue optionally linked to basic and/or neutral nonhydrophobic amino acid residues; $R_2$ is one or more neutral nonhydrophobic amino acid residues; $R_3$ is one or more hydrophobic amino acid residues optionally linked to neutral nonhydrophobic amino acid residues; X is hydrogen or an N-protecting group; and Y is hydroxyl or a C-terminal protecting group. Examples are:

Lys Thr Lys Gly Ser Gly Phe Phe OCH$_3$
Arg Lys Thr Lys Gly Ser Gly Phe Phe OCH$_3$
Lys Thr Lys Gly Ser Gly Phe Phe Val Phe OCH$_3$
Lys Thr Lys Gly Ser Gly Phe Phe Val Phe OH
Pro Arg Lys Thr Lys Gly Ser Gly Phe Phe OCH$_3$
Lys Thr Lys Gly Ser Gly Phe Phe OH

15 Claims, No Drawings

PEPTIDES

This invention relates to certain peptides useful for desensitisation therapy, and to desensitisation compositions containing them.

It is well known that many substances are capable of releasing histamine from mast cells. Such release is often due to disruption of the cell membrane, and reagents behaving in this way are said to be non-selective. One of the physiological systems causing release of histamine involves attachment of an antibody to the cell surface. When the antibody reacts with its appropriate antigen, a process is initiated leading to release of histamine. It has been postulated that such antigen-antibody reaction causes distortion of the antibody molecule, so that a portion of it is brought into contact with the cell surface, thereby initiating the response. Release of histamine brought about in this fashion does not involve rupture of the cell membrane, and is said to be selective (see D. R. Stanworth, "Immediate Hypersensitivity", Chapter 8 North Holland Publishing Company London, 1973).

Experimentally, non-selective and selective release of histamine can be distinguished respectively by the presence or absence either of simultaneously released intracellular enzymes, or of radioactive chromium previously absorbed by the cell.

We now believe that substances capable of causing selective release of histamine may be used in desensitisation therapy of allergic humans.

An object of this invention is to provide a novel class of peptides having this property, and desensitisation compositions, particularly vaccines containing such peptides.

Accordingly the present invention provides a peptide of formula (I):

$$X\text{---}R\text{---}R_1\text{---}R_2\text{---}R_3\text{---}Y \qquad (I)$$

and salts thereof, consisting of 6 to 12 naturally occurring amino acid residues, wherein R is an optionally present group, capable of confering on a peptide resistance to enzyme breakdown; $R_1$ represents a residue of a basic amino acid, optionally linked to one or more residues of neutral non-hydrophobic amino acids and/or basic amino acids; $R_2$ represents a residue of a neutral non-hydrophobic amino acid, optionally linked to one or more further residues of neutral non-hydrophobic amino acids; $R_3$ represents a residue of a hydrophobic amino acid, optionally linked to one or more residues of neutral non-hydrophobic amino acids and/or hydrophobic amino acids; X is hydrogen, or a N-protecting group; and Y is hydroxyl, or a C-terminal protecting group.

Unless otherwise stated, the amino acids referred to hereafter are in the L- configuration.

When R is present, it is a group capable of confering on a peptide resistance to enzyme breakdown. Examples of suitable groups R are given in J. Rudinger, "The Design of Peptide Hormone Analogues", Chapter 9 in Drug Design, Volume (II) edited by E. J. Ariëns, Academic Press, New York and London, 1971.

Thus suitable examples of R, when present, include prolyl, hydroxyprolyl, the D- form of a common amino acid residue, or an amino acid residue with omission of the terminal amino group.

Suitable examples of $R_1$ include arginyl, lysyl and ornithyl and combinations of such residues, optionally with residue(s) of neutral non-hydrophobic amino acids such as threonyl and seryl. Particularly suitable examples of $R_1$ include Lys-Thr-Lys, Arg-Lys-Thr-Lys and the like. Normally $R_1$ will consist of 1 to 5 amino acid residues, suitably 3 to 5 residues. $R_1$ will often contain at least two basic amino acid residues and at least one neutral non-hydrophobic amino acid residue.

Suitable examples of neutral non-hydrophobic amino acids $R_2$ include glycyl, alanyl, seryl and threonyl and combinations of such residues. A particularly suitable example of $R_2$ is Gly-Ser-Gly. Preferably $R_2$ consists of 1 to 5 amino acid residues, for example 3 amino acid residues.

Suitable examples of hydrophobic amino acids $R_3$ include residues of amino acids notionally derived from alanine $\beta$-substituted by an aromatic or aliphatic hydrophobic group, such as phenylalanyl, valyl and leucyl; and combinations of such residues. Particularly suitable examples of $R_3$ include Phe-Phe and Phe-Phe-Val-Phe. Preferably $R_3$ consists of 1 to 4 amino acid residues, for example 2 or 4 residues.

X is hydrogen or a N-protecting group. Suitable examples of N-protecting groups X include those conventionally known for this use in peptide chemistry. Examples of such groups include carboxylic acid groups such as acetyl, chloroacetyl, trifluoroacetyl, butyryl, benzoyl, phenylacetyl, pyridine-carbonyl; or an acid group derived from carbonic acid such as ethoxycarbonyl, benzyloxycarbonyl, t-butyloxycarbonyl, biphenylisopropoxycarbonyl, p-methoxy-benzyloxycarbonyl, p-nitrobenzyloxycarbonyl, p-bromobenzyloxycarbonyl, p-phenylazobenzyloxycarbonyl, p-(p'-methoxyphenylazo)-benzyloxycarbonyl, t-amyloxycarbonyl; or an acid group derived from a sulphonic or p-toluenesulphonic acid; or other groups such as benzyl, trityl, formyl, phthaloyl, o-nitrophenylsulphenyl, benzylidene or nitro. Preferred N-protecting groups X include t-butyloxycarbonyl or benzyloxycarbonyl.

Suitable C- terminal protecting groups Y include ester residues, for example residues of $C_{1-6}$ alkyl esters such as methoxy, ethoxy and t-butoxy; benzyloxy, p-nitrobenzyloxy, p-methoxybenzyloxy; residues of trimethylsilyl esters; and residues of amides, substituted amides (e.g. amides substituted by one or two $C_{1-6}$ alkyl groups, or by a $C_{1-6}$ acyl group), and hydrazino residues. Preferred groups Y include hydroxyl and methoxy.

The peptides of the invention have 6 to 12 amino acid residues. Preferably they have 8 to 10 amino acid residues.

One particularly suitable group of peptides is of formula (II):

$$X\text{---}R\text{---}[b\text{-}c\text{-}d\text{-}e]\text{---}[f\text{-}g\text{-}h]\text{---}[i\text{-}j\text{-}k\text{-}l]\text{---}Y \qquad (II)$$

wherein X, Y and R are as defined; c and e are lysyl, arginyl or ornithyl; d is threonyl or seryl; b is an optionally present arginyl; lysyl or ornithyl; f and h are glycyl or alanyl; g is seryl or threonyl; i and j are phenylalanyl, valyl or leucyl; and k and l are optionally present phenylalanyl, valyl or leucyl; and salts thereof.

Preferably in formula (II) X is hydrogen and Y is hydroxyl, —$NH_2$ or $C_{1-4}$ alkoxy such as methoxy, and, when R is present, it is prolyl or hydroxyprolyl.

Examples of peptides within the scope of the invention are:

Lys Thr Lys Gly Ser Gly Phe Phe—$Y^1$

Arg Lys Thr Lys Gly Ser Gly Phe Phe—Y¹
Lys Thr Lys Gly Ser Gly Phe Phe Val Phe—Y¹
Arg Lys Thr Lys Gly Ser Gly Phe Phe Val Phe—Y¹
Pro Arg Lys Thr Lys Gly Ser Gly Phe Phe—Y¹
Pro Arg Lys Thr Lys Gly Ser Gly Phe Phe Val Phe—Y¹ wherein Y¹ is hydroxyl, —NH₂ or methoxy.

The peptides of this invention may be prepared by methods known in the art of peptide synthesis comprising coupling the amino acids from which the peptide is derived sequentially to build up the desired peptide.

Methods of sequential coupling of amino acids to form peptides by forming amide links are well known in the art. In general the amino acids, provided with protecting groups where necessary, are coupled in the correct order, or smaller peptides are combined into larger units. The amide linkage is usually prepared by condensing an amino acid, or peptide, having a protected α-amino group and a free or activated terminal carboxyl group, with an amino acid or peptide with a protected carboxyl group and a free α-amino group.

Activation of the carboxyl group can be effected, for example, by converting the carboxyl group into an acid halide, an azide, anhydride or imidazole, or into an activated ester such as the cyanomethyl ester, p-nitrophenyl ester, 2,4,5-trichlorophenyl ester, pentachlorophenyl ester, N-hydroxysuccinimide ester, benztriazole ester.

The most widely used methods of condensation of amino acids or peptides include the carbodiimide method, the azide method, the anhydride method, and the activated esters method, as described, for example, by Schroder and Lubke in "The Peptides", Volume 1 (1969), (Academic Press). An alternative method is the solid phase method of Merrifield (J. Am. Chem. Soc., 85, 2149 (1963)).

Any reactive groups in the amino acid or peptide which are not to take part in the condensation reaction should be protected by any of the N-protecting groups or carboxyl protecting groups described above which can be readily removed after the condensation.

The removal of the protecting group(s) present in the resultant peptide may be effected by an appropriate procedure depending upon the kind(s) of the protective group(s). Some typical procedures are as follows: hydrogenation in the presence of palladium catalyst (e.g. palladium carbon, palladium black) for benzyloxycarbonyl, p-nitrobenzyloxycarbonyl, p-bromo-benzyloxycarbonyl, p-phenylazobenzyloxycarbonyl, p-(p'-methoxyphenylazo)-benzyloxycarbonyl and trityl groups protecting the amino end; treatment with hydrogen bromide in glacial acetic acid for benzyloxycarbonyl, p-bromobenzyloxycarbonyl, p-phenylazobenzyloxycarbonyl and t-butyloxycarbonyl groups protecting the amino end; treatment with metallic sodium in liquid ammonia for benzyloxycarbonyl, p-bromobenzyloxycarbonyl and tosyl groups protecting the amino end; treatment with hydrochloric acid and/or acetic acid for trityl, t-butyloxycarbonyl, formyl and benzylidene groups protecting the amino end; treatment with alkali for methyl, ethyl and benzyl esters protecting the carboxyl end; treatment with acid for methyl, ethyl, benzyl, p-methoxybenzyl and t-butyl esters protecting the carboxyl end; and hydrogenation in the presence of palladium catalyst for benzyl and p-nitrobenzyl esters protecting the carboxyl end.

Acid addition salts of compounds of formula (I) are included within this invention, for example the salts of pharmaceutically acceptable acids as a hydrohalide, especially the hydrochloride or hydrobromide; or the phosphate, acetate, phenylpropionate, maleate, tartrate and citrate.

The peptides and salts of the present invention may be employed as the active agents in desensitisation vaccines. Such vaccines are well known to those skilled in the art and comprise a sterile liquid vehicle in which the active agent is dissolved or suspended. If suspended, the particles of active agent should be small enough not to block the orifice of an injection needle. Certain adjuvants such as tyrosine are often included in such vaccine compositions and are believed to provide a support and prolonged slow release of active material in vivo. Usually a patient receiving treatment with such desensitisation vaccines is administered a number of injections, spread over a period of weeks or days, each injection containing a higher concentration of active agent than the preceding one. In this way the patient is desensitised such that his allergic reaction to allergens is reduced or eliminated.

An alternative mode of administration for desensitisation agents is by application to the nasal mucosa as a liquid spray or as a dry powder snuff.

Yet another possible route of administration would be by application to the buccal mucosa, again as a liquid or dry composition.

Accordingly, the present invention includes a pharmaceutical composition adapted for use in desensitisation therapy, comprising a peptide or pharmaceutically acceptable salt of formula (I) together with a pharmaceutically acceptable carrier suitable for parenteral, intra-nasal or buccal administration.

A preferred composition of the invention is a desensitisation vaccine.

The compositions of the invention may be administered in conventional manner for desensitisation therapy.

The preparation and properties of some of the peptides of this invention are illustrated by the following examples.

Peptides were synthesised by classical methods of peptide synthesis described in the literature of peptide chemistry, for example by means of classical solution synthesis or solid phase peptide synthesis (SPPS), or by use of a combination of these methods.

Where appropriate amino acids refer to the L-configuration unless otherwise stated, and the following abbreviations are used:

| | |
|---|---|
| Boc Tert-Butyloxycarbonyl | BAW Butanol:Acetic Acid: water |
| Bzl Benzyl | CHCL₃ Chloroform |
| Z Benzyloxycarbonyl (carbobenzoxy) | MES Morpholine Ethyl Sulphonic Acid |
| OTcP 2,4,5 Trichlorophenyl ester | EtAc Ethyl Acetate |
| DMF Dimethylformamide | MeOH Methanol |
| Et₃N Triethylamine | EtOh Ethanol |
| DCCI Dicyclohexylcarbodiimide | —OMe Methyl ester |
| THF Tetrahydrofuran | AcOH Acetic Acid |
| OSu N hydroxysuccinimide ester | HCL Hydrochloric Acid |
| OBz Benzyl ester | TLC Thin Layer Chromatography |
| M.D.C. Methylene dichloride | M.P. Melting Point |
| Rf Ratio of product distance: solvent front distance, from point of application | NMR Nuclear Magnetic Resonance |
| c Number of grams per 100mls | T.F.A. Trifluoroacetic acid |
| [α]ᴅ²⁵ Specific rotation at 25° C. using sodium light (the D line) | p.Tsa p-Toluensulphonate |
| | R.T. Room Temperature |

EXAMPLE 1

The preparation of LysThrLysGlySerGlyPhePheOMe

The octapeptide methyl ester was prepared by a 4+4 fragment condensation strategy, one fragment (I) being prepared by solid phase peptide synthesis (SPPS) (according to SPPS Manual by J. M. Stewart and J. D. Young Freeman and Company San Francisco 1969) and the other fragment (II) by classical solution synthesis. Combination of I and II gave fully protected octapeptide (III) which on deprotection afforded the desired product (V).

(I) BOC Lys(Z)Thr(Bzl)Lys(Z)Gly N₂H₃

This intermediate was prepared by SPPS, employing standard DCCI mediated coupling procedures using a 0.47 mM/g glycine substituted Merrifield Resin. The fully protected tetrapeptide-resin was cleaved by treatment with 100 equivalents of hydrazine hydrate in DMF at room temperature for 3 days. Standard work-up gave I in good yield. This was crystallised from EtOH/water and then EtAc; m.p. 132°–134° C.; TLC homogeneous in 9:1 CHCl₃: MeOH/I₂ stain with Rf 0.44; NMR consistent with structure; $[\alpha]_D^{25} = -1.3°$ (C=1, DMF); amino acid analysis:

required: 1.00 Thr: 1.00 Gly: 2.00 Lys.
found: 1.00 Thr: 1.05 Gly: 2.01 Lys.

(II) Ser(Bzl)GlyPhePheOMe.HCl

The tetrapeptide methyl ester hydrochloride was prepared by solution synthesis in six stages.

(i) BOC-Phe.Phe.OMe

BOC-Phe-OSu (5.25 g, 0.0145 M) was coupled to Phe.OMe.HCL (3.13 g, 0.0145 M) in DMF (25 ml) in the presence of 1 equivalent of Et₃N (2.03 ml) at room temperature over 3 days. The reaction mixture was poured into water (250 ml) and the product extracted into EtAc (100 ml). It was isolated in 81% (5.00 g) yield and crystallisation from petrol (b.pt. 80°–100° C.) gave a m.p. of 123°–124° C.; $[\alpha]_D^{25} = -11.0°$ (C=1, DMF).

(ii) Phe.Phe.Ome.HCl:

The intermediate (i) (4.65 g) was BOC-deprotected using a solution of 2 N HCL in EtAc (30 ml) over 2 hours at room temperature. The product precipitated from solution in 78% yield (3.10 g) and had m.p. 205° C.; $[\alpha]_D^{25} = 43.3°$ (C=1, AcOH).

(iii) BOC.Gly.Phe.Phe.OMe

BOC.Gly.OSu (2.18 g, 0.008 M) was coupled to (ii) (2.90 g, 0.008 M) in DMF in the presence of 1 equivalent of Et₃N (1.12 ml) at room temperature over 3 days. Similar work-up described for isolation of (i), gave the product in 67% yield (2.60 g); m.p. 159°–161° C., after crystallisation from EtAc (40 ml) $[\alpha]_D^{25} = -9.5°$ (C=1, DMF); amino acid analysis:

required: 1.00 Gly: 2.00 Phe.
found: 1.00 Gly: 2.02 Phe.

(iv) GlyPhePheOMe.HCl

The intermediate (iii) (2.60 g) was BOC-deprotected in a similar manner to that described for (ii). The product deposited as an oil which was triturated with ether to give a white crystalline solid in almost quantitative yield. The material was purified further on Sephadex LH20 column eluting with water and had m.p. 196°–199° C.; TLC in 9:1 CHCl₃: MeOH showed one spot with I₂ stain at Rf. 0.22. Amino acid analysis:

required: 1.00 Gly: 2.00 Phe.
found: 1.00 Gly: 1.94 Phe.

(v) BOC.Ser(Bzl)GlyPhePheOMe

BOC.Ser(Bzl)OH (1.66 g, 0.0056 M) was coupled to (iv) (2.36 g, 0.0056 M) in MDC (20 ml) at 0° C. using DCCI (1.16 g, 0.0056 M) and Et₃N (0.79 ml: 1 equivalent). The reaction mixture was stirred at 0° C. for ½ hour, room temperature for 2 hours, filtered and filtrate evaporated in vacuo. Crystallisation of the residue from EtAc/petrol (80°–100° C.) afforded a 67% yield (2.50 g) of product, m.p. 163°–167° C. TLC in 9:1 CHCl₃: MeOH (I₂ stain) showed product at Rf 0.68; $[\alpha]_D^{25} = -13.0°$ (C=1, DMF). The NMR spectruum was consistent with structure. Amino acid analysis:

required: 1.00 Ser: 1.00 Gly: 2.00 Me.
found: 0.94 Ser: 1.12 Gly: 2.00 Phe.

(vi) Ser(Bzl)GlyPhePheOMe.HCl (II):

Intermediate (v) (1.75 g) above was BOC-deprotected in a similar manner to that described for (ii). Addition of ether to the reaction mixture gave product as a solid in 96% yield (1.52 g), $[\alpha]_D^{25} = 21.0°$ (C=1, AcOH). It was purified on Sephadex LH20 eluting with 1 M AcOH, $[\alpha]_D^{25} = 21.0°$ (C=1, AcOH) TLC examination in 9:1 CHCl₃: MeOH (I₂ stain) showed product (acetate salt) as one spot at Rf 0.27. The NMR spectrum was consistent with structure. Amino acid analysis:

required: 1.00 Ser: 1.00 Gly: 2.00 Phe.
found: 1.00 Ser: 1.11 Gly: 1.92 Phe.

(III) BOC.Lys(Z)Thr(Bzl)Lys(Z)GlySer(Bzl)GlyPhePheOMe

Tertiaryl-butyl nitrite (0.32 ml, 0.00266 M) was added with vigorous stirring to a solution of (I) (1.60 g, 0.00177 M) in DMF (30 ml) containing 60 equivalents 2 N HCL in THF (5.5 ml, 0.0011 M) at −20° C. After 30 minutes, (II) (1.05 g, 0.00177 M) in DMF (5 ml) with sufficient Et₃N (2.11 ml) present to neutralise all HCl present, was added, and the reaction mixture stirred for 18 hours at 4° C., filtered and filtrate concentrated in vacuo. Addition of cold water gave product which was obtained in 50% yield (1.28 g) after crystallisation from EtOH. TLC in 9:1 CHCl₃:MeOH (I₂ stain) was homogeneous and showed product at Rf 0.6. M.p. 202°–203° C.; $[\alpha]_D^{25} = -5.9°$ (C=1, DMF). The NMR spectrum was consistent with structure. Amino acid analysis:

required: 2.00 Lys: 2.00 Phe: 2.00 Gly: 1.00 Thr: 1.00 Ser.
found: 2.00 Lys: 1.94 Phe: 2.06 Gly: 0.99 Ser: 0.96 Thr.

(IV) Lys(Z)Thr(Bzl)Lys(Z)GlySer(Bzl)GlyPhePheOMe.HCl

Fully protected octapeptide (II) (1.20 g) was BOC-deprotected in 2 N HCl solution in a 6:14 DMF/EtAc solvent mixture (20 ml). Prolonged reaction time of 4 hours was used at room temperature and addition of ether deposited product. Recrystallisation from MeOH/ether gave a 52% yield (0.60 g) of product. TLC in 9:1 CHCl$_3$: MeOH (I$_2$ stain) showed one major spot at Rf 0.4; $[\alpha]_D^{25} = 10.1°$ (C=1, AcOH). Amino acid analysis:

required: 1.00 Thr: 1.00 Ser: 2.00 Gly: 2.00 Phe: 2.00 Lys.
found: 1.00 Thr: 1.00 Ser: 2.17 Gly: 2.19 Phe: 2.32 Lys.

(V) LysThrLysGlySerGlyPhePheOMe

Partially protected octapeptide (IV) (0.10 g) was hydrogenated in 85% AcOH (70 ml) with 10% Pd/C catalyst (0.20 g) over a steady stream of hydrogen for 20 hours. The mixture was filtered, evaporated in vacuo and residue filtered on Sephadex LH20 eluting with water to give the desired octapeptide methyl ester (V) (0.03 g, 46% yield). TLC examination showed 1 spot at Rf 0.2 in 5:2:2 BAW (t-BuOCl/KI-starch stain) and Rf 0.5 in 5:2:3 BAW (Ninhydrin stain). Amino acid analysis:

required: 1.00 Ser: 1.00 Thr: 2.00 Gly: 2.00 Phe: 2.00 Lys.
found: 1.00 Ser: 1.03 Thr: 2.02 Gly: 2.06 Phe: 1.98 Lys.

Isotachophoretic examination showed one band in >95% amount (leading electrolyte 10 mM KOH+MES pH 6.0 and terminating electrolyte 10 mM β-alanine and HCl pH 4.23). The NMR 80 HzFT spectrum was consistent with structure.

EXAMPLE 2

The preparation of ArgLysThrLysGlySerGlyPhePheOMe

This nonapeptide was prepared by coupling of (IV) above with Z.Arg(Z)$_2$.OSu, followed by hydrogenolysis of the resultant fully protected nonapeptide.

(i) Z.Arg(Z)$_2$Lys(Z)Thr(Bzl)Lys(Z)GlySer(Bzl)GlyPhePheOMe:

To octapeptide (IV) (0.344 g, 0.30025 M) above in DMF (3 ml) at 0° C. was added (1 equivalent) Et$_3$N (0.025 g in 1 ml DMF) and Z-Arg(Z)$_2$OSu (0.17 g, 0.00025 M in 2 ml DMF). The solution was left at 4° C. for 65 hours, diluted with water (8 ml) and the deposited product filtered off and dried (0.37 g, 78% yield). Crystallisation from DMF/EtOH gave product with m.p. 204°–210° C. (decomposition). TLC examination in 9:1 CHCl$_3$: MeOh (I$_2$ stain) showed on U.V. visualisation 1 spot at Rf 0.69. The NMR spectrum was consistent with structure. Amino acid analysis:

required: 1.00 Thr: 1.00 Ser: 2.00 Gly: 2.00 Phe: 2.00 Lys: 1.00 Arg.
found: 1.00 Thr: 1.00 Ser: 2.10 Gly: 2.01 Phe: 2.04 Lys: 1.04 Arg.

(ii) ArgLysThrLysGlySerGlyPhePheOMe

Fully protected nonapeptide (i) (0.07 g) above was dissolved in a minimum amount of DMF and 5 times the volume of AcOH added. The mixture was hydrogenated in the presence of 10% Pd/C catalyst (2.5 times weight of compound) for 19 hours at room temperature using a steady stream of hydrogen. Water was added to give a 15% aqueous solution and the mixture hydrogenated for a further 3 hours. Filtration and evaporation in vacuo at 45° C. gave product as a glassy solid. Purification was performed on a Sephadex LH20 column eluting with 1 M AcOH and product isolated in 26% yield (0.018 g). TLC in 5:3:5 BAW (ninhyrin stain) showed product at Rf 0.34. Amino acid analysis:

required: 1.00 Thr: 1.00 Ser: 2.00 Gly: 2.00 Phe: 2.00 Lys: 1.00 Arg.
found: 1.00 Thr: 1.01 Ser: 2.07 Gly: 2.00 Phe: 2.07 Lys: 1.00 Arg.

EXAMPLE 3

The preparation of LysThrLysGlySerGlyPhePheValPheOMe

The decapeptide methyl ester was synthesised by a 4+2+4 fragment condensation strategy as follows:

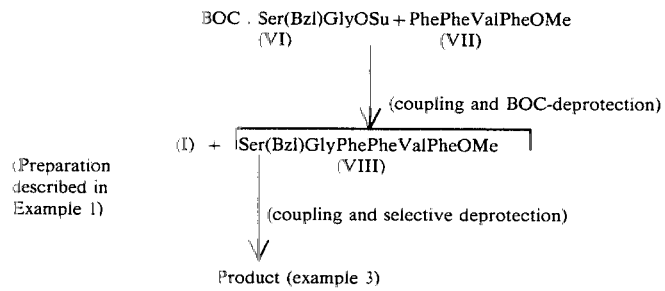

(Preparation described in Example 1)

(VI) BOC.Ser(Bzl)Gly.OSu

Prepared in three stages:

(i) BOC.Ser(Bzl)GlyOMe

BOC.Ser(Bzl)OH (5.0 g, 0.017 M) was coupled to Gly.OMe.HCl (2.13 g, 0.017 M) in M.D.C. (100 ml) at R.T. for 3½ hours in the presence of 1 equivalent of Et$_3$N and using DCCI (3.5 g, 0.017 M) as the condensing agent. The precipitate was filtered off and the solution washed X 2 with water, aqueous NaHCO$_3$, water, dried and evaporated in vacuo to leave an oil (7.1 g). T.L.C. 9:1 CHCl$_3$: MeOH (I$_2$ stain) showed one spot at Rf 0.64; $[\alpha]_D^{25\ C.} = 4.7°$ (C=1, MeOH).

(ii) BOC.Ser(Bzl)GlyOH

Compound (i) above (7.0 g) was dissolved in dioxan (25 ml) and treated with an equal volume of 1 N NaOH (25 ml) and the solution stirred for ½ hour at R.T. N HCl (25 ml) was added to a slight excess and the oil that formed extracted into EtAc. The organic layer was back-extracted into NaHCO$_3$ and acidified to pH 3.8 with 20% citric acid, extracted with EtAc, the organic layer washed with water, brine, dried and evaporated to leave the product as a syrup (4.0 g). T.L.C. 1:1 CHCl$_3$/EtOH (I$_2$ stain) showed product at Rf 0.59. The NMR spectrum was consistent with structure.

(iii) BOC.Ser(Bzl)GlyOSu

Compound (ii) above (4 g 0.01135 M) was treated with HOSu (1.3 g 0.011 M) and DCCI (2.34 g 0.011 M) in dioxan (50 ml) at R.T. overnight. The precipitate that formed was filtered off, solvent removed and the product crystallised from I.P.A. (100 ml) in 59% yield (3.00 g). T.L.C. 9:1 $CHCl_3$/MeOH ($I_2$ stain) showed one major spot Rf 0.57; M.P. 132°–134° C.; $[\alpha]_D^{25} = -1.8°$ (C=1, MeOH).

(VII) PhePheValPheOMe

Prepared in six steps:

(i) BOC.ValPheOMe

BOC.ValOSu (10.0 g, 0.0328 M) was coupled to PheOMe.HCl (6.85 g 0.0318 M) in toluene (2.00 ml) at room temperature overnight and in the presence of $Et_3N$ (1 equivalent). The mixture was filtered and filtrate washed with 1 N HCl, saturated NaCl solution, dried and evaporated in vacuo to give product (11.31 g) as a white crystalline compound in 94% yield. T.L.C. in 9:1 ($CHCl_3$:MeOH) ($I_2$ stain) shows one spot at Rf 0.77 $[\alpha]_D^{25} = -27.4°$ (C=1, MeOH).

(ii) ValPheOMe.HCl

Compound (i) (9.25 g) was BOC-deprotected in 2 N HCl in EtAc (100 ml) for 24 hours at room temperature when the product precipitated. The mix was diluted with dry EtAc and product filtered off in 78% yield (6.0 g). The product was finally purified on Sephadex LH20. M.P. 193°–193.5°; T.L.C. 9:1 $CHCL_3$/MeOH ($I_2$ stain) shows one spot at Rf 0.60. $[\alpha]_D^{25} = 63.3°$ (C=1, AcOH).

(iii) BOC.PheValPheOMe

Compound (ii) (5.34 g, 0.017 M) was coupled to BOC.PheOSu (6.15 g, 0.017 M) in 25% D.M.F. in Toluene (250 ml) at room temperature for 65 hours in the presence of $Et_3N$ (1 equiv.). The mixture was then filtered, solvent removed in vacuo and the syrup quenched with water. The white precipitated (8.5 g) was filtered off and recrystallised from EtAc/80°–100° petrol; yield 80%. T.L.C. 9:1 $CHCl_3$/MeOH ($I_2$ stain) shows one spot at Rf 0.69 $[\alpha]_D^{25} = -31.0°$ (C=1 MeOH). NMR consistent with structure.

(iv) PheValPheOMe.HCl

Compound (iii) (6.87 g) was BOC-deprotected in 2 N HCl in EtAc (100 ml) for 2 hours at room temperature when a white solid precipitated (5.84 g) representing 97% yield of product. M.P. 243°–245° (decomposition). T.L.C. in 9:1 $CHCl_3$:MeOH ($I_2$ stain) shows one spot at Rf 0.59. $[\alpha]_D^{25} = 8.8°$ (C=1, AcOH). (v) BOC.PhePheValPheOMe BOC.PheOSu (4.30 g 0.0119 M) was coupled to compound (iv) (5.5 g 0.0119 M) in toluene (100 ml) at room temperature for 65 hours in the presence of sufficient D.M.F. to produce solution, ant $Et_3N$ (1 equivalent). The solvent was evaporated in vacuo and the syrup quenched with water and product filtered off. The product was then triturated with hot ethanol, cooled and collected (6.38 g, 80% yield). M.P. 218°–219° C. T.L.C. in 9:1 $CHCl_3$:MeOH ($I_2$ stain) shows one spot at Rf 0.62. $[\alpha]_D^{25} = -15.9°$ (C=1, D.M.F.) The NMR spectrum was consistent with structure.

(vi) PhePheValPheOMe.Tfa

Compound (v) (5 g) was BOC-deprotected in T.F.A (25 ml) at 0° C. for ½ hour, and at room temperature for ½ hour. The solution was then quenched with ether (75 ml) and product filtered off (4.48 g, 88% yield). M.P. 224°–226° (decomposition). T.L.C. 9:1 $CHCl_3$:MeOH ($I_2$ stain) shows one spot at Rf 0.49. $[\alpha]_D^{25} = 10.6$ (C=1, AcOH). The NMR spectrum was consistent with structure.

(VIII) Ser(Bzl)GlyPhePheValPhe.OMe

Prepated in two stages:

(i) BOC.Ser(Bzl)GlyPhePheValPheOMe

Intermediate VI (2.37 g, 0.00528 M) was coupled to intermediate VII (3.62 g, 0.00528 M) in toluene (500 ml) overnight at room temperature in the presence of $Et_3N$ (0.74 ml, 0.00528 M). The mixture was washed with water, and solvent evaporated in vacuo. The solid obtained was triturated with water, dried and recrystallized from EtOH (4.42 g, yield 93%. T.L.C. 9:1 $CHCl_3$:MeOH ($I_2$ stain) shows one spot at Rf 0.61. $[\alpha]_D^{25°} = -13.5°$ (C=1 D.M.F.). The NMR spectrum was consistent with structure.

(ii) Ser(Bzl)GlyPhePheValPheOMe

Compound (i) (2.8 g) was BOC-deprotected in T.F.A. (30 ml) for 40 minutes at 0° C. The solution was quenched with ether (200 ml) and the precipitated product obtained in quantitative yield. T.L.C. 9:1 $CHCl_3$:MeOH ($I_2$ stain) shows one spot at Rf 0.2. M.P. 214°–216° C. (decomposition). $[\alpha]_D^{25°} = 3.7°$ (C=1, AcOH) The NMR spectrum was consistent with structure.

BOC.Lys(Z)Thr(Bzl)Lys(Z)GlySer(Bzl)GlyPhePheValPheOMe

Peptide I (2.25 g) (see Example 1) was coupled to VIII (2.19 g) by the Henzyl-Rudinger modification of the azide method, as previously described for the octapeptide. The product was recrystallized from EtOH and obtained in (2.5 g, 61% yield). M.P. 243°–244°. Amino acid analysis:
  calculated: 1Thr: 1Ser: 2GLy: 1Val: 3Phe: 2Lys.
  found: 1.13Thr: 1.11Ser: 2.15Gly: 1.00Val: 3.04Phe: 1.98Lys.
$[\alpha]_D^{25°} = -7.5°$ (C=1, D.M.F.). The NMR spectrum was consistent with structure.

LysThrLysGlySerGlyPhePheValPheOMe

The intermediate above (0.18 g) was BOC, Z and Bzl-deprotected by treatment with 33% HBr in dioxane (5 ml) at room temperature for 1 hour when a precipitate formed. Additional HBr/dioxan (5 ml) and water (1 ml) was then added which effected solution and reaction continued for a further ½ hour. Acetone (50 ml) was then added and the solution quenched with ether (100 ml). The supernatent was decanted and solid dissolved in water (7 ml) and freeze-dried to give 0.145 g product as the tri-hydrobromide salt. Amino acid analysis:
  required: 1Thr: 1Ser: 2Gly: 1Val: 3Phe: 2Lys.
  found: 1.05Ihr: 1.00Ser: 2.14Gly: 1.02Val: 3.13Phe: 2.00Lys.
An aliquot of product was purified on Sephadex LH20 eluting with water, to a one-spot material with Rf 0.384 (BAW 5:2:2, ninhydrin spray).

EXAMPLE 4

The preparation of LysThrLysGlySerGlyPhePheVal.
PheOH

The decapeptide free acid was synthesised by a 4+2+4 fragment condensation strategy as follows:

BOC . Ser(Bzl)GlyOSu   +   PhePheValPheOBz
(VI: preparation as in                    (IX)
Example 3)

(coupling and BOC-deprotection)

↓

ZLys(Z)Thr(Bzl) Lys(Z)GlyOTcp + Ser(Bzl)GlyPhePheValPheOBz
(XI)                                                    (X)

(coupling and complete deprotection)

↓

Product (example 4)

(IX) PhePheValPheOBz

Prepared in six stages:

(i) BOC.ValPheOBz

BOC.ValOSu (15.7 g, 0.050 M) was coupled to PheOBz.pTsa (21.35 g, 0.050 M) in dioxan (200 ml) at R.T. for 4½ hours in the presence of 1 equivalent of Et₃N. The reaction mixture was evaporated at reduced pressure and the resulting residue dissolved in EtAc and the solution washed with water, dried and evaporated in vacuo to leave a crystalline solid (21.3 g). T.L.C. 9:1 CHCl₃:MeOH (I₂ stain) showed one spot at Rf 0.93; $[\alpha]_D^{25°} = -31.8°$ (C=1, MeOH).

(ii) ValPheOBz.HCl

Compound (i) (21.3 g) was BOC-deprotected in 2 N HCl in EtAc (240 ml) for 4½ hours at R.T. when the product precipitated. The mix was diluted with dry ether and product filtered off in 78% yield (15.25 g). M.P. 180°–182°; T.L.C. 9:1 CHCl₃:MeOH (I₂ stain) shows one spot at Rf 0.44. $[\alpha]_D^{25°} = 24.4°$ (C=1, AcOH).

(iii) BOC.PheValPheOBz

Compound (ii) (15.25 g, 0.039 M) was coupled to BOC.PheOSu (14.13 g, 0.039 M) in 50% dioxan/DMF (450 ml) at R.T. for 4 hours in the presence of Et₃N (1 equivalent). The mixture was poured into iced water and the resulting white precipitate (20.0 g) was filtered off and recrystallised from EtAc/40°-60° petrol; yield 85%. M.P. 160°–162°. T.L.C. 9:1 CHCl₃:MeOH (I₂ stain) shows one spot at Rf 0.72. $[\alpha]_D^{25°} = -36.0°$ (C=1, MeOH).

(iv) PheValPheOBz.HCl

Compound (iii) (20.0 g, 0.033 M) was BOC-deprotected in 2 N HCl in EtAc (240 ml) for 2 hours at R.T. when a white solid precipitated (15.23 g) representing 85% yield of product. M.P. 228°–229° (decomposition). T.L.C. 9:1 CHCl₃:MeOH (I₂ stain) shows one spot at Rf 0.63. $[\alpha]_D^{25°} = -6.9°$ (C=1, AcOH).

(v) BOCPhePheValPheOBz

BOC.PheOSu (10.26 g, 0.0283 M) was coupled to compound (iv) (15.23 g, 0.0283 M) in 50% dioxan/DMF (250 ml) at R.T. for 4 hours in the presence of Et₃N (1 equivalent). The mixture was poured into iced water and the resulting white precipitate filtered off and recrystallised from EtAc/40°-60° petrol in quantitative yield (21.41 g). M.P. 191°–193°. T.L.C. 9:1 CHCl₃:MeOH (I₂ stain) shows one spot at Rf 0.72. $[\alpha]_D^{25°} = -12.8°$ (C=1, DMF).

(vi) PhePheValPheOBz.HCl

Compound (v) (21.15 g, 0.028 M) was BOC-deprotected in 2 N HCl in EtAc (500 ML) for 2 hours at R.T. The product (17.9 g) was precipitated in 92% yield upon addition of dry ether. M.P. 242° (decomposition). T.L.C. 9:1 CHCl₃:MeOH (I₂ stain) shows one spot at Rf 0.74. $[\alpha]_D^{25°} = -5.9°$ (C=1, AcOH). The NMR spectrum was consistent with structure.

(X) Ser(Bzl)GlyPhePheValPheOBz

Prepared in two stages:

(i) BOC.Ser(Bzl)GlyPhePheValPheOBz

Intermediate (VI) (4.49 g, 0.010 M) was coupled to intermediate (IX) (6.85 g, 0.010 M) in 35% DMF/dioxan (75 ml) at R.T. for 4 hours in the presence of Et₃N (1 equivalent). The mixture was poured into iced water and the precipitated product (9.39 g) recrystallised from methanol in 91% yield. M.P. 226°–228° C. T.L.C. 9:1 CHCl₃:MeOH (I₂ stain) shows one spot at Rf 0.74. $[\alpha]_D^{25°} = -13.0°$ (C=1, DMF). The F.T. ¹H NMR was consistent with structure.

(ii) Ser(Bzl)GlyPhePheValPheOBz.HCl

Compound (i) (5.0 g, 0.0051 M) was BOC-deprotected in 2 N HCl in EtAc (150 ml) for 2 hours at R.T. The product (4.42 g) was precipitated in 94% yield upon addition of dry ether. M.P. 232°–234° (decomposition). T.L.C. 9:1 CHCl₃:MeOH (I₂ stain) shows one spot at Rf 0.44. $[\alpha]_D^{25°} = -4.3°$ (C=1, AcOH). The NMR was consistent with structure.

(XI) ZLys(Z)Thr(Bzl)Lys(Z)GlyOTcp

Prepared in seven stages:

(i) BOC.Lys(Z)GlyOMe

BOC.Lys(Z)OSu (23.85 g, 0.050 M) was coupled to GlyOMe.HCl (6.25 g, 0.050 M) in 50% dioxan/DMF at R.T. for 4½ hours in the presence of 1 equivalent of Et₃N. The reaction mixture was evaporated in vacuo and the residue dissolved in EtAc. The solution was washed, dried, filtered and evaporated to a colourless oil which solidified on standing in 89% yield. T.L.C. 9:1 CHCl₃:MeOH (I₂ stain) showed one spot at Rf 0.54.

(ii) Lys(Z)GlyOme.HCl

Compound (i) (20.00 g, 0.0443 M) was BOC-deprotected in 2 N HCl in EtAc (250 ml) for 2 hours at R.T. when the product precipitated. The mixture was diluted with dry ether and the product filtered off in 96% yield (15.67 g). M.P. 158°-159°. T.L.C. EtAc (I$_2$ stain) showed one spot at Rf 0.52.

(iii) BOC.Thr(Bzl)Lys(Z)GlyOMe

BOC.Thr(Bzl)OH (6.18 g, 0.020 M) was coupled to compound (ii) (7.76 g, 0.020 M) in 30% DMF/dioxan (75 ml) in iced water for 1 hour then at R.T. for a further 2 hours in the presence of DCCI (1 equivalent) and Et$_3$N (1 equivalent). The reaction mixture was filtered and evaporated in vacuo and the residue purified by silica column chromatography eluting with chloroform. The product was isolated as a colourless solid in 49% yield. M.P. 135°-136°. T.L.C. 9:1 CHCl$_3$:MeOH (I$_2$ stain) showed one spot at Rf 0.57. The F.T. $^{13}$C NMR was consistent with structure.

(iv) Thr(Bzl)Lys(Z)GlyOMe.HCl

Compound (iii) (3.48 g, 0.0054 M) was BOC-deprotected in 2 N HCl in EtAc (100 ml) for 2 hours at R.T. The product (2.88 g) was precipitated in 91% yield upon addition of dry ether. M.P. 100°-101°. T.L.C. 9:1 CHCl$_3$:MeOH (I$_2$ stain) showed one spot at Rf 0.52. $[\alpha]_D^{25°} = -13.5°$ (C=1, AcOH).

(v) ZLys(Z)Thr(Bzl)Lys(Z)GlyOMe

ZLys(Z)OTcp (1.80 g, 0.003 M) was coupled to compound (iv) (1.72 g, 0.003 M) in dioxan (45 ml) at R.T. for 4 hours in the presence of Et$_3$N (1 equivalent). The product was filtered off, washed with water and dried in vacuo (1.36 g, 50% yield). M.P. 185°-188°. T.L.C. 9:1 CHCl$_3$:MeOH (I$_2$ stain showed one spot at Rf 0.76.

(vi) ZLys(Z)Thr(Bzl)Lys(Z)GlyOH

A solution of compound (v) (0.92 g, 0.001 M) in 50% DMF/methanol was treated with 1 N NaOH solution (2.5 ml) and stirred at R.T. for 1 hour. Upon acidification the precipitated product (0.45 g) was recrystallised from methanol in 49% yield. M.P. 171°-173°. T.L.C. 2:1 CHCl$_3$:MeOH (t.butyl chloroformate/NaI-starch spray) showed one spot at Rf 0.50 $[\alpha]_D^{25°} = -5.4°$ (C=1, AcOH). The F.T. $^{13}$C NMR was consistent with structure.

(vii) ZLys(Z)Thr(Bzl)Lys(Z)GlyOTcp

A solution of TcpOH (0.10 g, 0.0005 M) and compound (vi) (0.0005 M) in DMF was treated with DCCI (0.11 g, 0.0005 M) and stirred at 5° for 1 hour then at R.T. overnight. The reaction mixture was filtered and the product (0.60 g) isolated as a crispy solid upon evaporation in vacuo. M.P. 176°-178°. T.L.C. 9:1 CHCl$_3$:MeOH (I$_2$ stain) showed one spot at Rf 0.71. $[\alpha]_D^{25°} = -6.0°$ (C=1, AcOH).

ZLys(Z)Thr(Bzl)Lys(Z)GlySer(Bzl)GlyPhePheValPheOBz

Peptide (XI) (0.55 g, 0.0005 M) was coupled to compound (X) (0.46 g, 0.0005 M) in DMF at R.T. for 4 hours in the presence of Et$_3$N (1 equivalent). The reaction mixture was poured into iced water and the resulting precipitate filtered off and dried in vacuo. Purification by silica column chromatography, eluting with CHCl$_3$, gave the product (0.92 g) in 85% yield. T.L.C. 9:1 CHCl$_3$:MeOH (I$_2$ stain) showed one spot at Rf 0.34. The F.T. $^{13}$C NMR was consistent with structure.

LysThrLysGlySerGlyPhePheValPheOH

The intermediate above (0.76 g, 0.0003 M) was deprotected by continuous hydrogenation in 85% acetic acid with 1 N HCl (1 mM) for 18 hours in the presence of 10% Pd/charcoal (0.80 g). The product was purified on a Biogel P2 column eluting with 1 M ammonium acetate and subsequently on a CM32 cellulose column eluting with 0.1 M ammonium acetate pH5. Final isolation of the product in 23% yield was by lyopholisation. T.L.C. butanol/acetic acid/water (5:2:2) (ninhydrin spray) showed one spot at Rf 0.22. Amino acid analysis:
calculated: 2Lys: 1Thr: 2Gly: 1Ser: 3Phe: 1Val
found: 1.80Lys: 0.92Thr: 2.00Gly: 1.07Ser: 3.24Phe: 0.91Val

EXAMPLE 5

The preparation of ProArgLysThrLysGlySerGlyPhe PheOMe

This decapeptide was synthesised by a 1+1+4+4 fragment condensation strategy as follows:

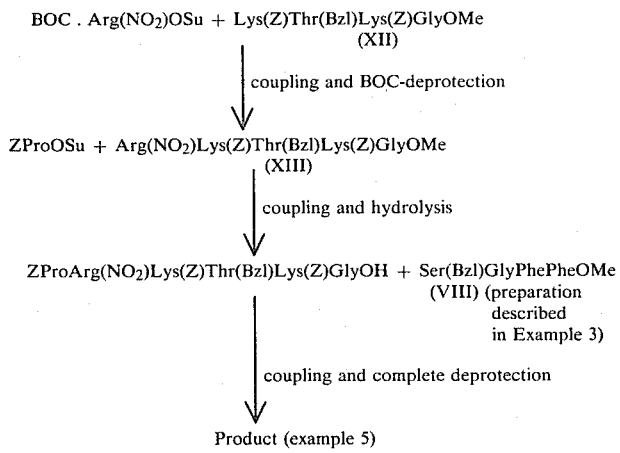

BOC . Arg(NO$_2$)OSu + Lys(Z)Thr(Bzl)Lys(Z)GlyOMe
(XII)

↓ coupling and BOC-deprotection

ZProOSu + Arg(NO$_2$)Lys(Z)Thr(Bzl)Lys(Z)GlyOMe
(XIII)

↓ coupling and hydrolysis

ZProArg(NO$_2$)Lys(Z)Thr(Bzl)Lys(Z)GlyOH + Ser(Bzl)GlyPhePheOMe
(VIII) (preparation described in Example 3)

↓ coupling and complete deprotection

Product (example 5)

(XII) LyS(Z)Thr(Bzl)Lys(Z)GlyOMe

Prepared in two steps from Thr(Bzl)Lys(Z)GlyOMe described in example 4.

(i) BOC.Lys(Z)Thr(Bzl)Lys(Z)GlyOMe

BOC.Lys(Z)OSu (2.38 g, 0.005 M) was coupled to Thr(Bzl) Lys(Z)GlyOMe.HCl (2.87 g, 0.005 M) in dioxan (60 ml) at R.T. for 4 hours in the presence of Et$_3$N (1 equivalent). The reaction mixture was poured into iced water to give the required product (3.80 g) as a crystalline white solid in 84% yield. M.P. 103°–105°. T.L.C. 9:1 CHCl$_3$:MeOH (I$_2$ stain) showed one spot at Rf 0.55. $[\alpha]_D^{25°} = -10.4°$ (C=1, AcOH).

(ii) Lys(Z)Thr(Bzl)Lys(Z)GlyOMe.HCl

Compound (i) (3.80 g, 0.0042 M) was BOC-deprotected in 2 N HCl in EtAc (100 ml) for 2 hours at R.T. The product (3.30 g) was precipitated in 93% yield upon addition of dry ether. M.P. 184°–186°. T.L.C. 9:1 CHCl$_3$:MeOH (I$_2$ stain) showed one spot at Rf 0.30. $[\alpha]_D^{25°} = 5.6°$ (C=1, AcOH).

(XIII) Arg(NO$_2$)Lys(Z)Thr(Bzl)Lys(Z)GlyOMe

Prepared in two stages:

(i) BOC.Arg(NO$_2$)Lys(Z)Thr(Bzl)Lys(Z)GlyOMe

BOC.Arg(NO$_2$)OSu (1.40 g, 0.0033 M) was coupled to compound (XII) (3.30 g, 0.004 M) in 10% DMF/dioxan (55 ml) at R.T. for 3 hours in the presence of Et$_3$N (1 equivalent). Unreacted (XII) was filtered off and the reaction mixture poured into iced water, extracted with EtAc to give the product (2.60 g) which was recrystallised from IPA in 71% yield. M.P. 133°–135°. T.L.C. 9:1 CHCl$_3$:MeOH (I$_2$ stain) showed one spot at Rf 0.42. $[\alpha]_D^{25°} = -6.7°$ (C=1, AcOH).

(ii) Arg(NO$_2$)Lys(Z)Thr(Bzl)Lys(Z)GlyOMe.HCl

Compound (i) (2.0 g, 0.0018 M) was BOC-deprotected in 2 N HCl in EtAc (50 ml) for 2 hours at R.T. The product (1.75 g) was precipitated in 92% yield upon addition of dry ether. M.P. 157° (decomposition). T.L.C. 2:1 CHCl$_3$:MeOH (I$_2$ stain) showed one spot at Rf 0.53. $[\alpha]_D^{25°} = -5.6°$ (C=1, MeOH).

(XIV) ZProArg(NO$_2$)Lys(Z)Thr(Bzl)Lys(Z)GlyOH

Prepared in two stages:

(i) ZProArg(NO$_2$)Lys(Z)Thr(Bzl)Lys(Z)GlyOMe

ZProOsu (0.57 g, 0.0016 M) was coupled to compound (XIII) (1.71 g, 0.0016 M) in 20% DMF/dioxan (30 ml) at R.T. for 2 hours in the presence of Et$_3$N (1 equivalent). The reaction mixture was poured into iced water and extracted with EtAc to give the product (1.11 g) in 54% yields. T.L.C. 9:1 CHCl$_3$:MeOH (I$_2$ stain) showed one spot at Rf 0.36.

(ii) ZProArg(NO$_2$)Lys(Z)Thr(Bzl)Lys(Z)GlyOH

A solution of compound (i) (0.87 g, 0.0007 M) in 50% DMF/methanol (30 ml) was treated with 1 N NaOH solution (1.7 ml) and stirred at R.T. for 2 hours. Acidification precipitated the product (0.43 g) in 50% yield. T.L.C. 2:1 CHCl$_3$:MeOH (I$_2$ stain) showed one spot at Rf 0.77. $[\alpha]_D^{25°} = -4.1°$ (C=1, AcOH). The NMR was consistent with structure.

ZProArg(NO$_2$)Lys(Z)Thr(Bzl)Lys(Z)GlySer(Bzl)- GlyPhePheOMe

Peptide (XIV) 0.40 g, 0.0033 M) was coupled to compound (VIII) (0.20 g, 0.0034 M) in DMF (5 ml) in the presence of Et$_3$N (1 equivalent), DCCI (0.07 g, 0.0035 M) and hydroxybenzotriazole (0.044 g, 0.0035 M) at 5° for 1 hour then at R.T. for 1 hour. The precipitated urea was filtered off and the required product (0.50 g) isolated by pouring the reaction mixture into iced water and isolating by filtration in 88% yield. T.L.C. 9:1 CHCl$_3$:MeOH (I$_2$ stain) showed one spot at Rf 0.52. The NMR was consistent with structure.

ProArgLysThrLysGlySerGlyPhePheOMe

The intermediate above (0.40 g, 0.0022 M) was deprotected by continuous hydrogenation in 85% acetic acid for 18 hours in the presence of 10% Pd/charcoal catalyst (0.40 g). The product was purified on a Biogel P2 column eluting with water and subsequently on an LH20 Sephadex column again with aqueous elution. Final isolation of the product in 34% yield was by lyopholisation. T.L.C. butanol/acetic acid/water (5:2:2) (ninhydrin spray) showed one spot at Rf 0.34. Amino acid analysis
calculated: 1Pro: 1Arg: 2Lys: 1Thr: 2Gly: 1Ser: 2Phe
found: 0.95Pro: 0.99Arg: 1.88Lys: 1.00Thr: 2.00Gly: 1.01Ser: 1.96Phe.

EXAMPLE 6

The preparation of LysThrLysGlySerGlyPhePheOH

The octapeptide free acid was synthesised by a 4+4 fragment condensation strategy as follows:

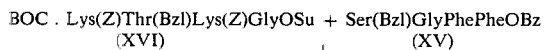

BOC . Lys(Z)Thr(Bzl)Lys(Z)GlyOSu + Ser(Bzl)GlyPhePheOBz
(XVI)                                   (XV)

(coupling and complete deprotection)

Product (example 6)

(XV) Ser(Bzl)GlyPhePheOBz

Prepared in six stages:

(i) BOCPhePheOBz

BOCPheOH (11.88 g, 0.045 M) was coupled to PheOBz.pTsa 19.4 g, 0.045 M) in MDC (200 ml) at 0° for 1 hour then at R.T. overnight in the presence of Et$_3$N (1 equivalent) and DCCI (1 equivalent). The reaction mixture was filtered and the product (14.92 g) isolated in 64% yield upon evaporation in vacuo and recrystallisation from EtOAc/80°–100° petrol (14.92 g). M.P. 123.5°–124.5°. T.L.C. 1:1 EtAC: 80°–100° petrol (I$_2$ stain) showed one spot at Rf 0.68. $[\alpha]_D^{25°} = -16.7°$ (C=1, MeOH).

(ii) PhePheOBz.Tfa

Compound (i) (14.0 g, 0.028 M) was BOC-deprotected in 50% Tfa in MDC (100 ml) for ½ hour at 0°. The solution was quenched with dry ether and the product (14.23 g) filtered off in quantitative yield. M.P. 180° (decomposition). T.L.C. 9:1 CHCl$_3$:MeOH (I$_2$ stain) showed on spot at Rf 0.73. $[\alpha]_D^{25°} = 17.5°$ (C=1, AcOH).

(iii) BOCGlyPhePhe OBz

BOC.GlyOSu (9.6 g, 0.0353 M) was coupled to compound (ii) (18.20 g, 0.0353 M) in toluene, MDC and DMF (125 ml) at R.T. overnight in the presence of Et$_3$N (1 equivalent). The reaction mixture was evaporated at reduced pressure and the resulting residue dissolved in EtAc, washed, dried and evaporated in vacuo to leave a crystalline solid (19.71 g) in quantitative yield. M.P. 127°–130°. T.L.C. 9:1 CHCl$_3$:MeOH (I$_2$ stain) showed one spot at Rf 0.81. $[\alpha]_D^{25°} = -17.4°$ (C=1, MeOH).

(iv) GlyPhePheOBz.Tfa

Compound (iii) (19.3 g, 0.0346 M) was BOC-deprotected in 50% Tfa in MDC (130 ml) for 1½ hours at 0°. The solution was quenched with ether and the product (17.79 g) filtered off in 90% yield. T.L.C. 9:1 CHCl$_3$:MeOH (I$_2$ stain) showed single spot at Rf 0.35. $[\alpha]_D^{25°} = 6.0°$ (C=1, AcOH).

(v) BOC.Ser(Bzl)PhePheOBz

BOC.Ser(Bzl)OSu (11.03 g, 0.0282 M) was coupled to compound (iv) (16.13 g, 0.0282 M) in 15% DMF/toluene (350 ml) at R.T. overnight in the presence of Et$_3$N (1 equivalent). The reaction mixture was evaporated at reduced pressure and the resulting residue dissolved in EtAc, washed, dried and evaporated in vacuo to give the product (14.88 g) in 72% yield upon recrystallisation from EtAc/petrol. M.P. 149°-151°. T.L.C. 9:1 CHCl$_3$:MeOH (I$_2$ stain) showed a single spot at Rf 0.65. $[\alpha]_D^{25°} = -11.2°$ (C=1, MeOH).

(vi) Ser(Bzl)GlyPhePheOBz

Compound (v) (14.45 g, 0.0196 M) was BOC-deprotected in 50% Tfa in MDC (140 ml) for 1 hour at 0°. The solution was quenched with ether and the product (13.1 g) filtered off in 89% yield. M.P. 185°-187° (decomposition). T.L.C. 9:1 CHCl$_3$:MeOH (I$_2$ stain) showed one spot at Rf 0.43. $[\alpha]_D^{25°} = 10.1°$ (C=1, AcOH).

(XVI)BOC.Lys(Z)Thr(Bzl)Lys(Z)GlyOSu

Prepared in four stages from BOC.Thr(Bzl)Lys(Z)GlyOMe described in example 5.

(i) Thr(BZl)Lys(Z)GlyOMe.Tfa

BOC.Thr(Bzl)Lys(Z)GlyOMe (2.87 g, 0.0045 M) was BOC-deprotected in 50% Tfa in MDC (50 ml) for 1 hour at 0°. The solution was quenched with ether and the product (2.10 g) filtered off in 72% yield. T.L.C. 9:1 CHCl$_3$:MeOH (I$_2$ stain) showed one spot at Rf 0.26.

(ii) BOC.Lys(Z)Thr(Bzl)Lys(Z)GlyOMe

BOC.Lys(Z)OSu (2.00 g, 0.003 M) was coupled to compound (i) (1.45 g, 0.003 M) in 10% DMF/toluene at R.T. overnight.
The reaction mixture was evaporated at reduced pressure and the resulting residue dissolved in EtAc, washed, dried and evaporated in vacuo to give the product (2.04 g) in 74% yield upon recrystallisation from EtAc/petrol. M.P. 117°-119°. T.L.C. 9:1 CHCl$_3$:MeOH (I$_2$ stain) showed one spot at Rf 0.60.

(iii) BOC.Lys(Z)Thr(Bzl)Lys(Z)GlyOH

A solution of compound (ii) (1.98 g, 0.0022 M) in DMSO (30 ml) was treated with 1 N NaOH solution (1½ equivalents) and stirred at R.T. for 1 hour. Acidification gave the product (1.82 g) in quantitative yield. T.L.C. 5:1 CHCl$_3$:MeOH (I$_2$ stain) showed compound just above baseline.

(iv) BOC.Lys(Z)Thr(Bzl)Lys(Z)GlyOSu

HOSu (0.24 g, 0.002 M) was coupled to compound (iii) (1.82 g, 0.002 M) in dioxan (25 ml) at R.T. for 4 hours in the presence of DCCI (1 equivalent). The reaction mixture was filtered and the filtrate evaporated at reduced pressure. Recrystallisation of the residue from EtOH gave the product (0.30 g) in 15% yield. M.P. 118°-122°. T.L.C. 9:1 CHCl$_3$: MeOH (I$_2$ stain) showed one spot at Rf 0.50. $[\alpha]_D^{25°} = -4.0°$ (C=1, DMF). The NMR was consistent with structure.

BOC.Lys(Z)Thr(Bzl)Lys(Z)GlySer(Bzl)GlyPhePheOBz

Peptide (XVI) (0.22 g, 0.0023 M) was coupled to compound (XV) (0.17 g, 0.0023 M) in 5% DMF/toluene (21 ml) at R.T. overnight in the presence of Et$_3$N (1 equivalent). The reaction mixture was evaporated at reduced pressure and the residue recrystallised from EtOH to give the product (0.29 g) in 85% yield. M.P. 195°-199°. T.L.C. 9:1 CHCl$_3$:MeOH (I$_2$ stain) showed one spot at Rf 0.67. The NMR was consistent with structure.

LysThrLysGlySerGlyPhePheOH

The intermediate above (0.25 g, 0.0017 M) was dissolved in Tfa (10 ml) and deprotected by bubbling through HBr at R.T. for 1 hour. The solution was quenched with dry ether and the product dried in vacuo over P$_2$O$_5$ and KOH. The product was purified on a Biogel P2 column eluting with water and subsequently on a CM32 cellulose column eluting with a linear ionic strength gradient of ammonium acetate pH5 which gave separation of the free acid and some benzyl ester contaminant. Final isolation of the product was by lyopholisation. T.L.C. butanol/acetate acid/water (5:2:2) (ninhydrin spray) showed one spot at Rf 0.20. Amino acid analysis:

calculated: 2 Lys: 1Thr: 2Gly: 1Ser: 2Phe
found: 1.77Lys: 0.96Thr: 2.00Gly: 1.06Ser: 2.1Phe

Biological Activity

Biological results obtained for Example 1-6 in three different assay systems are presented in Tables 1 and 2.

As is apparent from Table 1, the peptides were capable of releasing histamine selectively from rat mast cells in vitro, and producing histamine release effects in rat and baboon skin in vivo. In the latter case in particular (primate tissue) activity was ususually high.

Table 2 demonstrates cross-desensitisation in rat mast cells in vitro between the peptides of Example 3 and an antigen.

Table 1

Histamine Release Effects of Synthetic Peptides (Examples 1-6)

| PEPTIDE | SYSTEM | No.of Exps. | ACTIVITY | LDH/$^{51}$Cr Release | Inhibition of Activity |
|---|---|---|---|---|---|
| LysThrLysGlySer-GlyPhePheOMe (Example No. 1) | Rat Mast Cells invitro[1] | 7 | $7.5 \times 10^{-6}$M | None at $10^{-6}$M | 50% Inhibition by Intal ($10^{-4}$in vitro |
|  | Rat Skin in vivo[2] | 2 | $1.0 \times 10^{-4}$M |  |  |
|  | Baboon Skin in vivo[3] | 2 | $5.0 \times 10^{-7}$M |  |  |
| ArgLysThrLysGly- | Rat Mast Cells | 7 | $1.5 \times 10^{-7}$M |  |  |

Table 1-continued
Histamine Release Effects of Synthetic Peptides (Examples 1-6)

| PEPTIDE | SYSTEM | No. of Exps. | ACTIVITY | LDH/$^{51}$Cr Release | Inhibition of Activity |
|---|---|---|---|---|---|
| SerGlyPhePheOMe (Example No. 2) | in vitro[1] | | | | |
| | Rat Skin in vivo[2] | 2 | $1.0 \times 10^{-4}$M | | |
| | Baboon Skin in vivo[3] | 2 | $1.0 \times 10^{-7}$M | | |
| LysThrLysGlySerGly-PhePheValPheOMe (Example No. 3) | Rat Mast Cells in vitro[1] | 10 | $1.0 \times 10^{-6}$M | None at $10^{-4}$M peptide | |
| | Rat Skin in vivo[2] | 5 | $1.0 \times 10^{-5}$M | | |
| | Baboon Skin in vivo[3] | 14 | $1.0 \times 10^{-8}$M | | Partial Inhibition by Antihistamine or Intal-like drug |
| LysThrLysGlySer-GlyPhePheValPhe (Example No. 4) | Rat Mast Cells in vitro[1] | 2 | $3.3 \times 10^{-5}$M | | |
| | Rat Skin in vivo[2] | 4 | $1.0 \times 10^{-4}$M | | |
| | Baboon Skin in vivo[3] | 2 | $1.0 \times 10^{-5}$M | | |
| ProArgLysThrLysGly-SerGlyPhePheOMe (Example No. 5) | Rat Mast Cells in vitro[1] | 2 | $9.2 \times 10^{-6}$M | | |
| | Rat Skin in vivo[2] | 4 | $1.0 \times 10^{-4}$M | | |
| | Baboon Skin in vivo[3] | 2 | $1.0 \times 10^{-7}$M | | |
| LysThrLysGly-SerGlyPhePhe (Example No. 6) | Rat Mast Cells in vitro[1] | 4 | $1.0 \times 10^{-5}$M | | |
| | Rat Skin in vivo[2] | 4 | $1.0 \times 10^{-4}$M | | |
| | Baboon Skin in vivo[3] | 3 | $1.0 \times 10^{-5}$M | | |

[1] The average concentration of peptide to give approximately 50% release of available histamine from rat mast cells in a number of experiments.
[2] The average concentration of peptide to give an end point inintradernal titrations in rat skin in a number of experiments.
[3] The average concentration of peptide to give an end point inintradernal titrations in baboon skin in a number of experiments.

Table 2
Cross Desensitisation between Antigen and BRL 21547 Peptide of Example 3) in the Rat Mast Cell System

| Desensitiser | Desensitisation Steps | | | | Challenge | Total average % histamine release |
|---|---|---|---|---|---|---|
| | 1 | 2 | 3 | 4 | | |
| Buffer | Buffer | Buffer | Buffer | Buffer | Buffer | 4 |
| | Buffer | Buffer | Buffer | Buffer | BRL 21547 ($10^{-5}$M) | 47 |
| | Buffer | Buffer | Buffer | Buffer | XOA 1µg/ml | 56 |
| BRL 21547 | $5 \times 10^{-8}$M | $10^{-7}$M | $5 \times 10^{-7}$M | $10^{-6}$M | Buffer | 6 |
| | $5 \times 10^{-8}$M | $10^{-7}$M | $5 \times 10^{-7}$M | $10^{-6}$M | BRL 21547 ($10^{-5}$M) | 6 |
| | $5 \times 10^{-8}$M | $10^{-7}$M | $5 \times 10^{-7}$M | $10^{-6}$M | XOA 1µg/ml | 17 |
| XOA | 0.005 (µg/ml) | 0.01 | 0.05 | 0.1 | Buffer | 6 |
| | 0.005 (µg/ml) | 0.01 | 0.05 | 0.1 | BRL 21547 ($10^{-5}$M) | 6 |
| | 0.005 (µg/ml) | 0.01 | 0.05 | 0.1 | XOA 1µg/ml | 6 |

Methods (a) (1) Histamine, (2) $Cr^{51}$ and (3) Lactic Dehydrogenase Release from Rat Peritoneal Mast Cells (Rat Mast Cell in vitro test)

Mast cells, derived from the peritoneal washings of three male, outbred Wistar rates (250–300 g), were purified by the procedure according to Cooper and Stanworth (Preparative biochem. 4(2), 105, 1975).

The purified cells were washed twice in Dulbecco's incomplete (i.e. free from mineral salts) buffer and then resuspended in Dulbecco's medium to the required volume. In a typical experiment, sufficient cells were available for 30 duplicate challenges, i.e. 60 samples and in this case the resuspension volume employed was 6.1 mls. 0.1 ml of cell suspension were taken for estimating the cell count.

(1) Histamine release

One third of the cell suspension was employed. To 0.9 ml duplicate aliquots of challenge solution, prepared in complete Dulbecco's medium and prewarmed to 37° C., was added 0.1 ml of cell suspension. The solutions were then shaken gently, and allowed to incubate for 5 minutes at 37° C. The reaction tubes were then quickly removed from the incubator and placed in an ice bath. Supernatants were then seqparated from the cell population following centrifugation for 3 minutes at 1000 r.p.m. The cell residues were then treated with 2 mls of 0.4 N perchloric acid and allowed to stand for approximately 30 minutes at ambient temperature. The precipitated protein was removed by centrifugation and the supernatant solutions set aside for histamine analysis. The original supernatant solutions were treated with 1.0 ml of 0.8 N perchlorate and then treated in a similar manner to the cell residues. Histamine was measured by the method according to Evans, Lewis and Thompson (Life Sciences, 12, 327, 1973) using a Technicon Autoanalyser. Histamine release was calculated as a percentage of total histamine available in each challenge solution.

(2) $Cr^{51}$ release

One third of the cell suspension was employed. To approximately 2.0 ml of cell suspension in Dulbecco's medium was added 0.1 ml of a solution of $Cr^{51}$ labelled sodium chromate. Approximately 50–100 $\mu$Ci $Cr^{51}$ was employed (specific activity: 300–500 $\mu$Ci/mg Cr). The cells were allowed to stand for 30 minutes at ambient temperature and then excess chromium was removed by washing the cells three times in Dulbecco's buffer. The cell pellet was finally resuspended in the same buffer and 0.1 ml of cell suspension was then added to 0.9 ml of each challenge solution, prewarmed to 37° C. After 5 minutes' incubation the cell suspensions were removed from the water bath and the supernants separated by centrifugation. Activity present in the whole recovered supernatants was measured using a Tracer Laboratory Spectromatic $\gamma$ counter. The percentage of $Cr^{51}$ released was assessed in relation to the values obtained for the positive and negative control solutions.

(3) LDH measurement

One third of the cell suspension was employed. The incubation procedure was identical to that described above and carried out simultaneously until the challenge solution supernatants were separated from the cell residues. Lactic dehydrogenase activity was then estimated directly in the supernatant solutions by the method according to Johnson and Erdös (Proc. Soc. Exp. Biol. Med. 142. 1252. 1973). To 0.5 ml of supernatant was added 0.5 ml of NAD (1 mM in 0.2 M Tris buffer, pH 8.5). 0.5 ml of this solution was then taken and treated with 50 $\mu$l of lactic acid (50 mM in 0.2 M Tris buffer, pH 8.5); as control 50 $\mu$l of 0.2 M Tris buffer (pH 8.5) was added to a second aliquot (0.5 ml) of the NAD solution. The solutions were incubated at ambient temperature for 20 minutes and the fluorescence emission was then measured. The excitation and emission wave lengths used were 340 and 460 nm respectively. All measurements were carried out using a Baird Atomic automatic spectrofluorimeter (Fluoripoint). The LDH activity was assessed in terms of the increase of fluorescence over control due to NADH formation following lactate addition. The percentage of LDH released was assessed in relation to the fluorescence intensity obtained in the positive control challenge solution supernatants (i.e. Triton $\times$ 100 challenge).

(b) Skin Test Method

Skin tests were carried out in the shaved backs of animals (rats and baboons) immediately after intravenous injection of pontamine sky blue (5%) in aqueous sodium chloride solution (0.9%) at a dose of 0.1 ml per kilogram of body weight in the case of rats and 5 ml per animal in the case of baboons.

Peptide in aqueous sodium chloride solution (0.9%), or saline control, were injected intradernally in 0.05 ml or 0.10 ml volumes. Skin reactions were read 20 minutes after intradernal challenge.

(c) Cross Desensitisation in the vitro rat mast cell system between antigen and peptide Brown Norway rats were immunised intraperitoneally with 100 $\mu$g of ovalbumen (XOA) in 1mg 'alum'. On day 27, peritoneal mast cells were removed, bulked and washed. Aliquots of cells were desensitised by the addition of 4$\times$5 minute incubations with various XOA or peptide concentrations or buffer alone. The cells were then submitted to an optimal histamine releasing challenge of peptide, XOA, or challenged with buffer alone.

We claim:

1. A peptide or a salt thereof, said peptide being characterized by the presence of the sequence of from 6 to 12 amino acid residues $$-[(R_1)-(R_2)-(R_3)]-$$

wherein $R_1$ is (i) one or more basic natural amino acid residues selected from the group consisting of arginyl, lysyl and ornithyl or (ii) a group of one or more of said basic natural amino acid residues and one or more neutral, non-hydrophobic natural amino acid residues selected from the group consisting of glycyl, alanyl, seryl and threonyl;

$R_2$ is one or more of said neutral, non-hydrophobic natural amino acid residues; and $R_3$ is (i) one or more hydrophobic natural amino acid residues selected from the group consisting of phenylalanyl, valyl and leucyl or (ii) a group of one or more of said hydrophobic natural amino acid residues and one or more of said neutral, non-hydrophobic natural amino acid residues, said peptide having the formula:

$$X-(R)_n-[(R_1)-(R_2)-(R_3)]-Y$$

wherein

X is hydrogen or a terminal amino protecting group,

Y is hydroxy or a terminal carboxylic acid protecting group;

R is a group capable of conferring resistance to enzymatic breakdown of a peptide; selected from prolyl and hydroxyprolyl and n is 0 or 1.

2. A peptide according to claim 1 wherein n is 1 and R is selected from the group consisting of prolyl, hydroxyprolyl, a D-amino acid residue and an amino acid residue with the omission of the terminal amino group.

3. A peptide according to claim 1 wherein X is hydrogen and Y is hydroxyl, amino or methoxy.

4. A peptide according to claim 1 having from 8 to 10 amino acid residues.

5. A peptice according to claim 1 having the structure

X—R—[b-c-d-e]-[f-g-h]-[i-j-k-l]—Y wherein X, Y and R are as therein defined; c and e are lysyl, arginyl or ornithyl; d is threonyl or seryl; b is an optionally present arginyl, lysyl or ornithyl; f and h are glycyl or alanyl; g is seryl or threonyl; i and j are phenylalanyl, valyl or leucyl; and k and l are optionally present phenylalanyl, valyl or leucyl; and salts thereof.

6. A peptide according to claim 5 wherein X is hydrogen, Y is hydroxyl, amino or methoxy, and R when present is propyl or hydroxyprolyl.

7. A peptide according to claim 1 selected from the group consisting of:

Lys Thr Lys Gly Ser Gly Phe Phe—$Y^1$
Arg Lys Thr Lys Gly Ser Gly Phe Phe—$Y^1$
Lys Thr Lys Gly Ser Gly Phe Phe Val Phe—$Y^1$
Arg Lys Thr Lys Gly Ser Gly Phe Phe Val Phe—$Y^1$
Pro Arg Lys Thr Lys Gly Ser Gly Phe Phe—$Y^1$
Pro Arg Lys Thr Lys Gly Ser Gly Phe Phe Val Phe—$Y^1$ wherein $Y^1$ is hydroxyl, —$NH_2$ or methoxy.

8. A pharmaceutical composition, adapted for use in desensitisation therapy, comprising a peptide according to claim 1 or a pharmaceutically acceptable salt thereof, together with a pharmaceutically acceptable carrier, suitable for parenteral, intro-nasal or buccal administration.

9. A composition according to claim 8 in a form suitable for parenteral administration.

10. A peptide according to claim 8 which is Lys Thr Lys Gly Ser Gly Phe Phe-$Y^1$ wherein $Y^1$ is therein defined.

11. A peptide according to claim 8 which is Arg Lys Thr Lys Gly Ser Gly Phe Phe-$Y^1$ wherein $Y^1$ is therein defined.

12. A peptide according to claim 8 which is Lys Thr Lys Gly Ser Gly Phe Phe Val Phe-$Y^1$ wherein $Y^1$ is therein defined.

13. A peptide according to claim 8 which is Arg Lys Thr Lys Gly Ser Gly Phe Phe Val Phe-$Y^1$ wherein $Y^1$ is therein defined.

14. A peptide according to claim 8 which is Pro Arg Lys Thr Lys Gly Ser Gly Phe Phe-$Y^1$ wherein $Y^1$ is therein defined.

15. A peptide according to claim 8 which is Pro Arg Lys Thr Lys Gly Ser Gly Phe Phe Val Phe-$Y^1$ wherein $Y^1$ is therein defined.

* * * * *